(12) United States Patent
Wu et al.

(10) Patent No.: US 8,205,500 B2
(45) Date of Patent: Jun. 26, 2012

(54) SYSTEMS AND METHODS FOR INSPECTING AN OBJECT USING ULTRASOUND

(75) Inventors: Yanyan Wu, Schenectady, NY (US); Edward James Nieters, Burnt Hills, NY (US); Thomas James Batzinger, Burnt Hills, NY (US); Nicholas Joseph Kray, Blue Ash, OH (US); James Norman Barshinger, Scotia, NY (US); Jian Li, Rexford, NY (US); Waseem Ibrahim Faidi, Schenectady, NY (US); Prabhjot Singh, Guilderland, NY (US); Francis Howard Little, Cincinnati, OH (US); Michael Everett Keller, Mason, OH (US); Timothy Jesse Sheets, San Marcos, TX (US)

(73) Assignee: General Electric Company, Niskayuna, NY (US)

( * ) Notice: Subject to any disclaimer, the term of this patent is extended or adjusted under 35 U.S.C. 154(b) by 378 days.

(21) Appl. No.: 12/277,884

(22) Filed: Nov. 25, 2008

(65) Prior Publication Data

US 2010/0126277 A1    May 27, 2010

(51) Int. Cl.
  *G01N 29/44* (2006.01)
  *G01B 5/00* (2006.01)
(52) U.S. Cl. ............... 73/602; 73/620; 702/39
(58) Field of Classification Search ........... 73/602, 73/598, 599, 600, 618, 620, 634, 637, 627, 73/649; 702/39
See application file for complete search history.

(56) References Cited

U.S. PATENT DOCUMENTS

| | | | | |
|---|---|---|---|---|
| 4,689,675 A * | 8/1987 | Tchorbajian et al. | ......... | 348/442 |
| 5,475,613 A * | 12/1995 | Itoga et al. | ....................... | 702/39 |
| 5,774,568 A * | 6/1998 | Freneix | ......................... | 382/100 |
| 6,142,942 A * | 11/2000 | Clark | ........................... | 600/443 |
| 6,370,480 B1 * | 4/2002 | Gupta et al. | .................... | 702/39 |
| 7,216,544 B2 | 5/2007 | Vaccaro et al. | | |
| 7,234,355 B2 * | 6/2007 | Dewangan et al. | ............. | 73/622 |
| 7,328,620 B2 * | 2/2008 | Howard et al. | .................. | 73/602 |
| 7,357,014 B2 | 4/2008 | Vaccaro et al. | | |
| 7,434,468 B2 * | 10/2008 | Puckett | .......................... | 73/649 |
| 7,856,882 B2 * | 12/2010 | Jesmonth | ........................ | 73/618 |
| 7,865,316 B2 * | 1/2011 | Turner et al. | .................... | 702/39 |
| 7,874,990 B2 * | 1/2011 | Nair et al. | ...................... | 600/449 |
| 2007/0089479 A1 | 4/2007 | Vaccaro et al. | | |
| 2008/0196475 A1 | 8/2008 | Engelbart et al. | | |

OTHER PUBLICATIONS

Carmen Perez, Francisco Fernandez, Manuel Borras, Tecnatom, S.A., San Sebastian De Los Reyes, Madrid, Spain; "Automatic Analysis of UT Inspections in Aircraft Structures (Midas-Autodet Software)"; ECNDT 2006—Poster 13; 7pages.

* cited by examiner

*Primary Examiner* — J M Saint Surin
(74) *Attorney, Agent, or Firm* — Penny A. Clarke

(57) ABSTRACT

An ultrasound inspection system is provided for inspecting an object. The inspection system includes an ultrasound probe configured to scan the object and acquire a plurality of ultrasound scan data. The inspection system further includes a processor coupled to the ultrasound probe and configured to apply a transfer function to the ultrasound scan data to compensate for distortion of a plurality of ultrasound signals through the object and thereby generate a plurality of compensated ultrasound scan data, and to process the compensated ultrasonic scan data to characterize a feature in the object.

21 Claims, 3 Drawing Sheets

SYSTEMS AND METHODS FOR INSPECTING AN OBJECT USING ULTRASOUND

BACKGROUND

The invention relates generally to non-destructive evaluation (NDE) and more particularly, to non-destructive evaluation of an object using ultrasound.

A variety of NDE inspection modalities are available to inspect industrial components. These inspection modalities have their own advantages and limitations and are typically employed based on the type of components that needs to be inspected. For example, ultrasound (UT) inspection is widely employed for identifying delamination.

However, in certain applications, UT inspection sometimes over-estimates defect sizes leading to false calls. Such inaccurate inspection results are prominent when objects being inspected have anisotropic material properties, are made of multi-material (e.g., glue, plys and so forth), and have thick cross-sections. Differences in the speed of sound in a component with respect to the X, Y and Z axes due to anisotropic material properties and/or the internal structure of the component causes distortion to the sound beam. Moreover, certain probe orientations (e.g., tilted relative to the part being inspected) causes additional distortion with a circular beam at the front surface becoming oval. The operator measures the dimension of the indication (defect) and will reject the component if the size of the defect exceeds a predetermined threshold. However, for anisotropic components, an indication in an image may not be representative of the real size, shape, and/or location of the defect, thereby leading to false rejections. The false rejections, in turn, can lead to increased cost and potential revenue loss.

For example, UT inspection of composite materials can provide inaccurate results, since composite materials are fibrous and inhomogeneous. The characterization of defects (size, shape, and/or location of the defect) in thick composite objects via UT inspection is challenging due to the interaction of sound with the fiber matrix. Current approaches for composite UT inspection include using a universal amplitude threshold for UT data and comparing the indication depth and location with known defect inserts. Defect characterization is typically conducted on 2D UT C-Scans. However, these techniques may not provide accurate inspection results. Further, different UT scans looking at the same defect are not correlated. Other available inspection modalities and techniques also provide limited accuracy for inspecting components made of composite material. Although composite inspection is a relatively new area, there is a need for accurate inspection of composite materials due to the increasing use of composite materials.

It would therefore be desirable to provide a technique to obtain and accurately determine indication size, shape and/or location for UT inspection of anisotropic or composite material.

BRIEF DESCRIPTION

Briefly, in accordance with one aspect of the present invention, an ultrasound inspection system is provided for inspecting an object. The inspection system includes an ultrasound probe configured to scan the object and acquire a plurality of ultrasound scan data. The inspection system further includes a processor coupled to the ultrasound probe and configured to apply a transfer function to the ultrasound scan data to compensate for distortion of a plurality of ultrasound signals through the object and thereby generate a plurality of compensated ultrasound scan data, and to process the compensated ultrasonic scan data to characterize a feature in the object.

In accordance with another aspect of the present invention, an ultrasound inspection system is provided for inspecting an object. The inspection system includes an ultrasound probe configured to scan the object and acquire a plurality of ultrasound scan data from a plurality of orientations. The inspection system further includes a processor coupled to the ultrasound probe and configured to map the ultrasound scan data from each of the orientations onto a three-dimensional model of the object to generate a three-dimensional inspection model for the object, and to characterize a feature in the object based on the three-dimensional inspection model for the object.

In accordance with an additional aspect of the present invention, a method is provided for inspecting an object. The method provides for acquiring a plurality of ultrasound scan data via an ultrasound probe, adjusting the ultrasound scan data by applying a transfer function to the ultrasound scan data to generate a plurality of adjusted ultrasound scan data, and characterizing a feature in the object based on the adjusted ultrasound scan data. Systems and computer programs that afford such functionality may be provided by the present invention.

In accordance with a further aspect of the present invention, a method is provided for inspecting an object. The method provides for acquiring a plurality of ultrasound scan data from a plurality of orientations via an ultrasound probe, mapping the ultrasound scan data from each of the orientations onto a three-dimensional model of the object to generate a three-dimensional inspection model for the object, and characterizing a feature in the object based on the three-dimensional inspection model for the object. Here again, systems and computer programs affording such functionality may be provided by the present invention.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
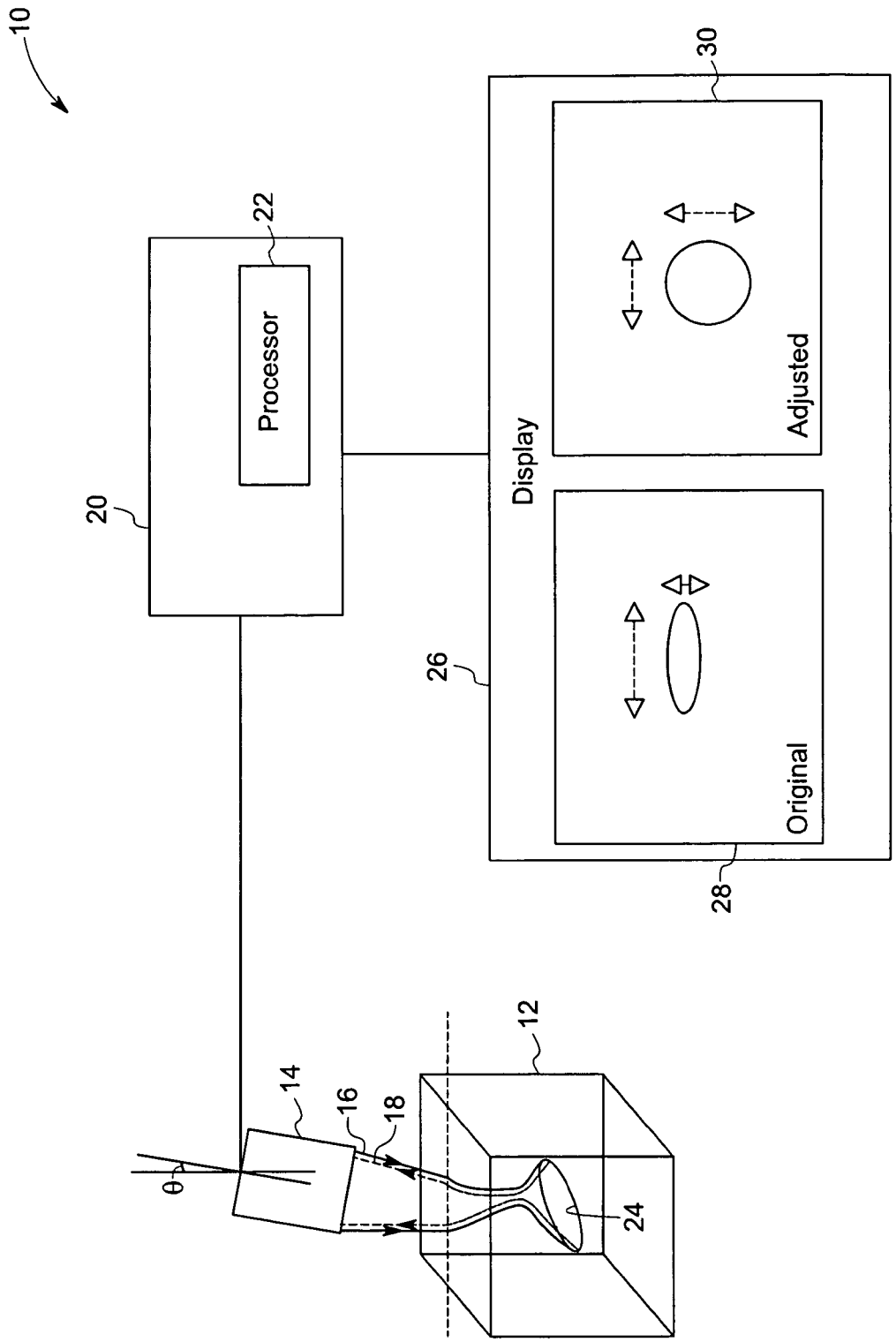
FIG. 1 depicts an exemplary ultrasound inspection system for inspecting an object.

FIG. 1 depicts an exemplary ultrasound inspection system 10 for inspecting an object 12 in accordance with aspects of the invention. Non-limiting examples of the object 12 include industrial parts, including but not limited to turbine airfoils, blades, disks, and shafts. The ultrasound inspection system 10 includes an ultrasound probe 14 for scanning the object 12 and acquiring ultrasound scan data. The ultrasound probe 14 acquires the ultrasound scan data by transmitting ultrasound signals 16 into the object 12 and receiving reflected echo signals 18 from the object 12. In certain embodiments, the probe 14 is configured to acquire the ultrasound scan data from multiple orientations. For example, the probe 14 may acquire the ultrasound scan data from the object 12 by scanning the object 12 normal to its surface, 0 degree tilted to the normal from one of the sides or either sides, 20 degree tilted to the normal from one of the sides or either sides, and so forth.

In the illustrated arrangement, the ultrasound system 10 further includes a console 20 coupled to the probe 14. The console 20 acts as an interface between the operator and the probe 14 and may control the operation of the probe 14. In the illustrated arrangement, the console 20 includes a processor 22 coupled to the ultrasound probe 14 and configured to process the ultrasound scan data acquired via the ultrasound probe 14 to characterize a feature 24 in the object 12. However, in other embodiments, the processor 22 may be disposed outside of the console 20. It should be noted that, in certain embodiments, the processor generates two-dimensional ultrasound images based on the reflected echo signals. Thus, the ultrasound scan data typically takes the form of a two-dimensional ultrasound images. In particular, the ultrasound scan data takes the form of a "c-scan," which is a two-dimensional colored or gray-scale ultrasound image, where color or gray-scale correspond to thickness of the object. The processor 22 then characterizes a feature 24 in the object 12 from the generated two-dimensional images. Non-limiting examples of the feature include a defect, such as a crack, a fissure, and so forth, in the object 12. In certain embodiments, characterizing the feature 24 of the object 12 includes measuring a size of the feature or identifying a shape or a location of the feature. The feature 24 is then displayed to an operator via a display device 26 coupled to the console 20. The ultrasound inspection system 10 may include other input/output devices to input the scanning/control parameters and to output the result. For example, the input/output devices may include keyboard, mouse, printer and so forth. The console 20 may further include various circuitries for interfacing with the probe 14 and input/output devices.

In certain embodiments, the processor 22 is configured to apply a transfer function to the ultrasound scan data to compensate for distortion of the ultrasound signals 16 through the object 12 and thereby generate a plurality of compensated ultrasound scan data. In particular, in certain embodiments, the processor applies the transfer function to the acquired two-dimensional ultrasound images 28 to compensate for distortion of the ultrasound signals 16 through the object 12 and thereby generate a plurality of compensated two-dimensional ultrasound images 30. It should be noted that the application of the transfer function may be based on an orientation of the ultrasound probe and/or a geometry of the object. In certain embodiments, the transfer function is applied to the ultrasound scan data from each of the plurality of orientations to compensate for distortion of the ultrasound signals through the object. The processor 22 then processes the compensated ultrasonic scan data to characterize the feature 24 in the object 12.

It should be noted that the processor 22 generates the transfer function based on at least one of ultrasound experimental data and ultrasound modeling data. The ultrasound experimental data comprises ultrasound distortion data within the material of the object 12 while the ultrasound modeling data comprises ultrasound sound behavior data within the material of the object 12. For example, in certain embodiments, the object comprises an anisotropic material, a composite material, and/or single crystal metals. The transfer function is therefore generated based on ultrasound distortion data and the ultrasound sound behavior data within the anisotropic material, the composite material, and/or single crystal metals.

In certain embodiment, the processor further transforms the compensated ultrasound scan data from one or more ultrasonic scans in a three-dimensional space to generate a three-dimensional representation of the object (a three-dimensional inspection model for the object). The transformation may be performed by fusing the compensated ultrasound scan data from the multiple ultrasonic scans onto a three-dimensional model of the object. The three-dimensional model of the object may include a three-dimensional computer aided design (CAD) model of the object, a three-dimensional mesh model of the object, a three-dimensional voxel model of the object, and so forth. These models contain detailed geometry and material information of ply structure (e.g., fiber orientation, ply thickness, ply shape) and ply material properties. All these information are employed for building the 3D sound propagation model inside the material of the object. The generated three-dimensional inspection model for the object may then be displayed on the display device 26.

Alternatively, in certain embodiment, the processor 22 is configured to map the ultrasound scan data from each of the orientations directly onto a three-dimensional model of the object 12 to generate a three-dimensional inspection model for the object. The processor 22 then characterizes a feature 24 in the object 12 based on the three-dimensional inspection model for the object 12. As discussed above, in certain embodiments, the transfer function is applied to the ultrasound scan data from each of the orientations to compensate for distortion of the ultrasound signals through the object. Such application of the transfer function may be based on the orientation of the ultrasound probe and/or the geometry of the object. Again, as discussed above, the generated three-dimensional inspection model for the object may then be displayed on the display device 26.

The exemplary ultrasound inspection system 10 may acquire images of the object under examination for subsequent inspection by a variety of techniques. In particular, as will be appreciated by those of ordinary skill in the art, control logic and/or automated routines for performing the techniques and steps described herein may be implemented by the inspection system 10 of FIG. 1, either by hardware, software, or combinations of hardware and software. For example, suitable code may be accessed and executed by the processor 22 to perform some or all of the techniques described herein. Similarly application specific integrated circuits (ASICs) configured to perform some or all of the techniques described herein may be included in the processor 22.

It should be noted that the present invention is not limited to any particular processor for performing the processing tasks of the invention. The term "processor," as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output. It should also be noted that the phrase "configured to" as used herein means that the processor is equipped with a combination of hardware and software for performing the tasks of the invention, as will be understood by those skilled in the art.

Figure 2:
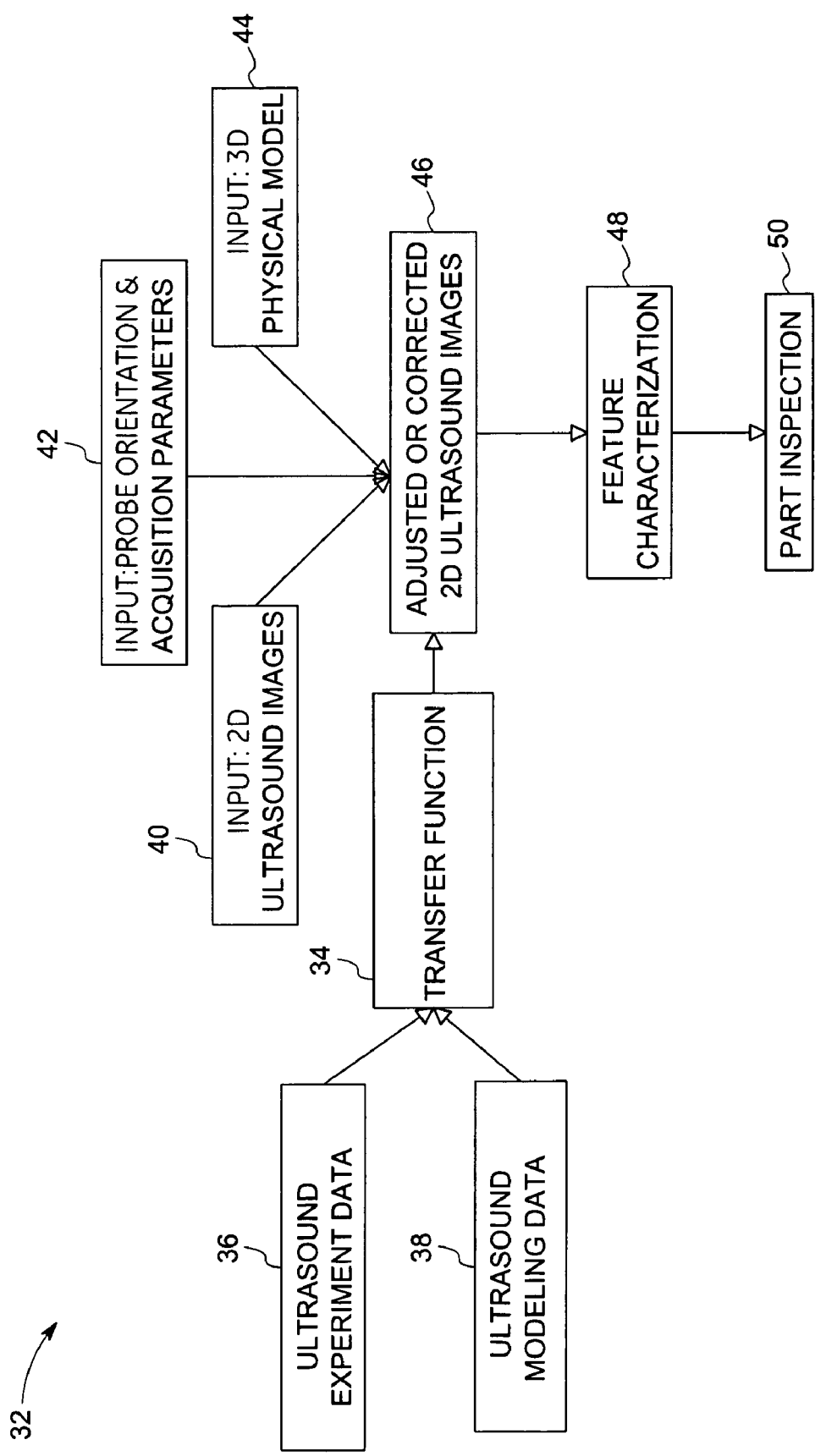
FIG. 2 is a flowchart illustrating a method of inspecting an object via the inspection system of FIG. 1.

For example, referring now to FIG. 2, an exemplary process 32 for inspecting an object is depicted via a flowchart in accordance with an embodiment of the invention. As illustrated in the flowchart, in the exemplary process 32, a transfer function 34 is generated for adjusting or correcting the ultrasound scan data. In particular, the generated transfer function adjusts or corrects the shapes, sizes and/or locations of the defects measured from the ultrasound scan data. The transfer function is derived based on at least one of ultrasound experimental data 36 and ultrasound modeling data 38. It should be noted that the ultrasound experimental data 36 comprises ultrasound distortion data within the material of the object and may be obtained by performing ultrasound scan experiments to study ultrasound distortion inside the material of the object. Similarly, the ultrasound modeling data 38 comprises ultrasound sound behavior data within the material of the object and may be obtained by performing ultrasound finite element analysis modeling to study the ultrasound sound behavior inside the material of the object.

The ultrasound scan data comprising multiple two-dimensional ultrasound images 40 of the object are acquired from multiple orientations via the ultrasound probe. The acquired two-dimensional ultrasound images 40 along with corresponding probe orientation and acquisition parameters 42 and a three-dimensional physical model 44 of the object are then provided as input parameters. The three-dimensional physical model 44 may be a predefined design model of the object in a three-dimensional modeling system, such as a CAD system. The transfer function 34 is then applied to the multiple two-dimensional ultrasound images 40 to generate corresponding corrected or adjusted two-dimensional ultrasound images 46. It should be noted that the application of the transfer function to correct the two-dimensional ultrasound images may be based on the orientation of the ultrasound probe with respect to the object and/or the geometry of the object.

Characterization of various features 48 in the object is then performed from the corrected or adjusted two-dimensional ultrasound images 46. Such characterization of features in the object may include measuring a size of the feature, identifying a shape of the feature, identifying a location of the feature, and so forth. As noted above, the feature may be a defect in the object, such as a crack or a fissure. In certain embodiments, the characterization of feature 48 may include detection of any defect and measurement of defect size, if any, from the corrected or adjusted two-dimensional ultrasound images 46. Finally, the process 32 may further include inspection 50 of the object based on the characterized feature to report deviations from the desired characteristics. In certain embodiments, the inspection 50 may include comparing the measured defect size to the specified defect limit or the tolerance limit. If the measured defect size exceeds the specified or tolerance limit, the inspected object is rejected.

Additionally, in certain embodiments, the ultrasound scan data from multiple orientations may be employed to create a three-dimensional representation of the object that is used as an inspection model for the object. The three-dimensional representation is generated by mapping and/or fusing the ultrasound scan data from multiple orientations onto a three-dimensional model of the object. The mapping and/or fusing may include performing at least one statistical analysis on the ultrasound scan data to determine redundant data and removing the redundant data from the three-dimensional inspection model based on the statistical analysis. Non-limiting examples of the statistical analysis include applying decision-making algorithms to determine the most accurate data. Non-limiting examples of decision-making algorithms include Bayesian Model and Neural Network algorithms. This three-dimensional representation is a substantially accurate model of the actual object and represents characteristics of the actual object, e.g. a manufactured or real object, rather than a theoretical or design model of the object. One or more feature in the object may then be characterized based on the three-dimensional representation of the object. It should be noted that, the ultrasound scan data may be original or adjusted two-dimensional ultrasound images.

Figure 3:
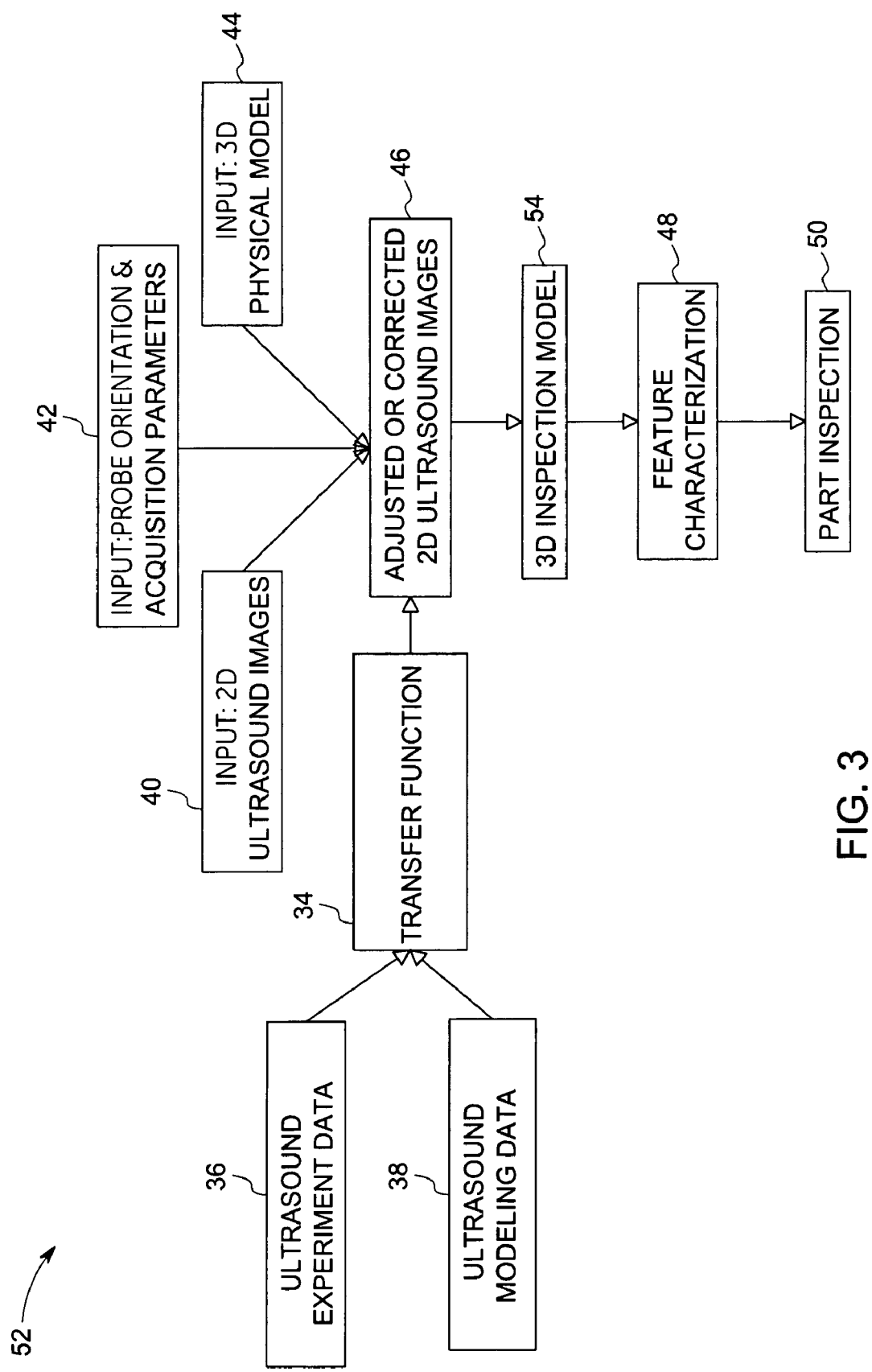
FIG. 3 is a flowchart illustrating another method of inspecting an object via the inspection system of FIG. 1.

For example, FIG. 3 depicts an exemplary process 52 for inspecting an object in accordance with another embodiment of the invention. In the exemplary process 52, the corrected or adjusted two-dimensional ultrasound images 46 from one or more ultrasonic scans are transformed in a three-dimensional space to generate a three-dimensional inspection model 54 for the object. The transformation comprises mapping and/or fusing the adjusted two-dimensional ultrasound images 46 from the one or more ultrasonic scans onto the three-dimensional physical model of the object 44. Various features 48 in the object are then characterized from the generated three-dimensional inspection model 54 for the object.

As will be appreciated by those skilled in the art, there are a variety of applications for the resulting three-dimensional inspection model for the object 12. For example, the three-dimensional inspection model for the object 12 may be further used for performing an engineering analysis, such as a finite element model (FEM) analysis. In this manner, the generated three-dimensional inspection model can be used to perform more accurate analyses on the object 12 to aid in engineering and design of improved components. In other example applications, the three-dimensional inspection model for the object 12 may be subsequently utilized to modify at least one of (a) a design of the component and (b) a manufacturing process for the object.

The ultrasound inspection system and inspection techniques described in various embodiments discussed herein efficiently and reliably obtain and determine indication size of thick composite material. The mapping of ultrasound inspection results onto a three-dimensional geometry with the signal correction reflecting the sound behavior inside composite accurately characterizes the defects and measures the defect size based on ultrasound data. The sensor hardware compensation to offset the signal distortion inside the composite further enhances the accuracy of the feature characterization. The fact that the present technique corrects the image generated for a composite part to account for the interaction between the ultrasonic sound path and the directions of the fibers within the composite material greatly enhances the reliability of the inspection result.

For example, in one application, the present technique would enable improvement of ultrasound inspection accuracy for composite fan blades. Currently, of the material scrapped, a significant proportion results from false calls due to ultrasound over-sizing. The present technique addresses this problem by significantly reducing false calls, such as oversizing of defects for composite parts (including composite fan blades, composite case), and thereby leading to significant cost savings.

Further, as will be appreciated by those skilled in the art, the transfer function derived from the ultrasound experimental data and the three dimensional ultrasound modeling data with detailed information about object's geometry and property may be utilized to optimize the ultrasound inspection or scan setups, including selecting the sensors, optimizing or planning the probe orientation and/or optimizing or planning probe scan path, so as to improve the inspection accuracy and reduce the inspection time.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An ultrasound inspection system for inspecting an object, the system comprising:

an ultrasound probe configured to scan the object and acquire a plurality of ultrasound scan data;

a processor coupled to the ultrasound probe and configured to apply a transfer function to the ultrasound scan data to compensate for distortion of a plurality of ultrasound signals through the object and thereby generate a plurality of compensated ultrasound scan data, and to process the compensated ultrasonic scan data to characterize a feature in the object, wherein the processor is configured to generate the transfer function based on at least one of a plurality of ultrasound experimental data and a plurality of ultrasound modeling data.

2. The ultrasound inspection system of claim 1, wherein the probe is configured to acquire the ultrasound scan data by transmitting the ultrasound signals into the object and receiving a plurality of reflected echo signals from the object.

3. The ultrasound inspection system of claim 1, wherein the processor is further configured to measure a size of the feature or identify a shape or a location of the feature.

4. The ultrasound inspection system of claim 1, wherein the object comprises a material, wherein the ultrasound experimental data comprises a plurality of ultrasound distortion data within the material, and wherein the ultrasound modeling data comprises a plurality of ultrasound sound behavior data within the material.

5. The ultrasound inspection system of claim 1, wherein the object comprises an anisotropic material or a composite material.

6. The ultrasound inspection system of claim 1, wherein the processor is further configured to transform the compensated ultrasound scan data from one or more ultrasonic scans in a three-dimensional space to generate a three-dimensional representation of the object.

7. The ultrasound inspection system of claim 6, wherein the processor is configured to perform the transform by fusing the compensated ultrasound scan data from the one or more ultrasonic scans onto a three-dimensional model of the object.

8. The ultrasound inspection system of claim 1, wherein the ultrasound probe is configured to acquire ultrasound scan data from a plurality of orientations.

9. The ultrasound inspection system of claim 1, wherein the processor is configured to apply the transfer function based on at least one of an orientation of the ultrasound probe and a geometry of the object.

10. An ultrasound inspection system for inspecting an object, the system comprising:

an ultrasound probe configured to scan the object and acquire a plurality of ultrasound scan data from a plurality of orientations;

a processor coupled to the ultrasound probe and configured to map the ultrasound scan data from each of the orientations onto a three-dimensional CAD model of the object, through a transfer function obtained by three-dimensional ultrasound modeling, to generate a three-dimensional inspection model for the object, and to characterize a feature in the object based on the three-dimensional inspection model for the object.

11. The ultrasound inspection system of claim 10, wherein the processor is further configured to fuse the ultrasound scan data from each of the orientations through decision-making algorithms.

12. The ultrasound inspection system of claim 10, wherein the processor is configured to apply the transfer function based on at least one of an orientation of the ultrasound probe and a geometry of the object.

13. The ultrasound inspection system of claim 10, further comprising a display device coupled to the processor for displaying the three-dimensional inspection model for the object.

14. A method for inspecting an object, the method comprising:

acquiring a plurality of ultrasound scan data via an ultrasound probe;

adjusting the ultrasound scan data by applying a transfer function to the ultrasound scan data to generate a plurality of adjusted ultrasound scan data, wherein said applying a transfer function is based on at least one of a plurality of ultrasound experimental data and a plurality of ultrasound modeling data; and characterizing a feature in the object based on the adjusted ultrasound scan data.

15. The method of claim 14, wherein characterizing comprises performing at least one of measuring a size of the feature or identifying a shape or a location of the feature.

16. The method of claim 14, wherein the object comprises a material, wherein the ultrasound experimental data comprises a plurality of ultrasound distortion data within the material, and wherein the ultrasound modeling data comprises a plurality of ultrasound sound behavior data within the material.

17. The method of claim 14, further comprising transforming the adjusted ultrasound scan data from one or more ultrasonic scans in a three-dimensional space to generate a three-dimensional representation of the object, wherein the transforming comprises fusing the adjusted ultrasound scan data from the one or more ultrasonic scans onto a three-dimensional model of the object.

18. The method of claim 14, wherein acquiring the ultrasound scan data comprises acuiring ultrasound scan data from a plurality of orientations.

19. The method of claim 14, wherein applying the transfer function is based on at least one of an orientation of the ultrasound probe and a geometry of the object.

20. A method for inspecting an object, the method comprising:

acquiring a plurality of ultrasound scan data from a plurality of orientations via an ultrasound probe;

mapping the ultrasound scan data from each of the orientations onto a three-dimensional CAD model of the object, through a transfer function obtained by three-dimensional modeling, to generate a three-dimensional inspection model for the object; and characterizing a feature in the object based on the three-dimensional inspection model for the object.

21. The method of claim 20, further comprising fusing the ultrasound scan data from each of the orientations through decision-making algorithms.

\* \* \* \* \*

UNITED STATES PATENT AND TRADEMARK OFFICE
CERTIFICATE OF CORRECTION

PATENT NO. : 8,205,500 B2  Page 1 of 1
APPLICATION NO. : 12/277884
DATED : June 26, 2012
INVENTOR(S) : Wu et al.

It is certified that error appears in the above-identified patent and that said Letters Patent is hereby corrected as shown below:

In Column 2, Line 67, delete "0" and insert --$\theta$--, therefor.

In Column 3, Line 1, delete "20" and insert --2$\theta$--, therefor.

In Column 8, Line 40, in Claim 18, delete "acuiring" and insert --acquiring--, therefor.

Signed and Sealed this
Twenty-second Day of January, 2013

David J. Kappos
*Director of the United States Patent and Trademark Office*